US011440065B2

(12) United States Patent
Oltz et al.

(10) Patent No.: US 11,440,065 B2
(45) Date of Patent: Sep. 13, 2022

(54) METHOD AND INSTALLATION FOR HANDLING MEDICAL WASTE COLLECTED IN A RECEPTACLE FOR MEDICAL WASTE, CATHERTER BAG FOR USE IN SUCH AN INSTALLATION AND MEDICAL WASTE MANAGEMENT SYSTEM

(71) Applicant: EVAC OY, Espoo (FI)

(72) Inventors: James Oltz, Cherry Valley, IL (US); Cody Bowers, Cherry Valley, IL (US); Chris Hawkins, Cherry Valley, IL (US); James Ehrlich, Cherry Valley, IL (US)

(73) Assignee: Evac Oy, Espoo (FI)

( * ) Notice: Subject to any disclaimer, the term of this patent is extended or adjusted under 35 U.S.C. 154(b) by 545 days.

(21) Appl. No.: 16/326,329

(22) PCT Filed: Aug. 17, 2017

(86) PCT No.: PCT/FI2017/050578
§ 371 (c)(1),
(2) Date: Feb. 18, 2019

(87) PCT Pub. No.: WO2018/033664
PCT Pub. Date: Feb. 22, 2018

(65) Prior Publication Data
US 2019/0184435 A1    Jun. 20, 2019

Related U.S. Application Data

(60) Provisional application No. 62/376,427, filed on Aug. 18, 2016.

(51) Int. Cl.
*B09B 3/00* (2022.01)
*A61M 1/00* (2006.01)
*E03D 5/00* (2006.01)
*E03C 1/18* (2006.01)
(Continued)

(52) U.S. Cl.
CPC .............. *B09B 3/0075* (2013.01); *A61M 1/73* (2021.05); *E03C 1/18* (2013.01); *E03C 1/182* (2013.01);
(Continued)

(58) Field of Classification Search
CPC ......... B09B 3/0075; E03C 1/182; E03D 5/00; E03D 5/105
(Continued)

(56) References Cited

U.S. PATENT DOCUMENTS

| 4,346,002 A | * | 8/1982 | Petzinger ................. C05F 3/04 |
|---|---|---|---|
| | | | 4/484 |
| 5,217,038 A | | 6/1993 | Pinder |

(Continued)

FOREIGN PATENT DOCUMENTS

| CN | 1518625 A | 8/2004 |
|---|---|---|
| CN | 2762768 Y | 3/2006 |

(Continued)

OTHER PUBLICATIONS

Chinese Search Report for related Application No. 2017800498184; reported on May 8, 2021.
(Continued)

*Primary Examiner* — Tuan N Nguyen
(74) *Attorney, Agent, or Firm* — von Briesen & Roper, s.c.

(57) ABSTRACT

A method and installation for handling medical waste, which is collected in a receptacle, includes a vacuum waste system (V), whereby medical waste is collected in the receptacle, medical waste is discharged from the receptacle into a waste fixture connected to a vacuum waste piping (13) of the vacuum waste system (V). The discharge sequence of the vacuum waste system discharges the medical waste from the waste fixture or the vacuum waste piping (13) of the vacuum waste system (V) to a waste collecting unit (20) of the vacuum waste system.

7 Claims, 1 Drawing Sheet

(51) Int. Cl.
    *E03D 5/10*         (2006.01)
    *E03C 1/182*      (2006.01)

(52) U.S. Cl.
    CPC ............... *E03D 5/00* (2013.01); *E03D 5/105* (2013.01); *B09B 3/00* (2013.01)

(58) Field of Classification Search
    USPC ........................................... 4/431, 479, 484
    See application file for complete search history.

(56) References Cited

U.S. PATENT DOCUMENTS

| | | |
|---|---|---|
| 5,885,240 A | 3/1999 | Bradbury et al. |
| 7,780,640 B1 | 8/2010 | Amador |
| 2005/0209585 A1 | 9/2005 | Nord et al. |

FOREIGN PATENT DOCUMENTS

| | | |
|---|---|---|
| CN | 2772461 Y | 4/2006 |
| CN | 201420286 Y | 3/2010 |
| CN | 203694195 U | 7/2014 |
| CN | 104370423 A | 2/2015 |
| CN | 204543034 U | 8/2015 |
| EP | 2133313 A2 | 12/2009 |

OTHER PUBLICATIONS

International Search Report for related International Application No. PCT/FI2017/050578; report dated Oct. 26, 2017.
Chinese Office Action for related Application No. 201780049818.4; reported on Aug. 18, 2021.

\* cited by examiner

METHOD AND INSTALLATION FOR HANDLING MEDICAL WASTE COLLECTED IN A RECEPTACLE FOR MEDICAL WASTE, CATHERTER BAG FOR USE IN SUCH AN INSTALLATION AND MEDICAL WASTE MANAGEMENT SYSTEM

TECHNICAL FIELD

The present invention relates to a method for handling medical waste or bio-waste, or other corresponding contaminated waste, which is collected in a receptacle for medical waste and to an installation therefor.

The method and installation can be employed in a hospital, medical center, or other corresponding institutions. The medical waste can originate from humans and animals.

BACKGROUND ART

Particularly in hospitals and medical institutions, medical human waste or bio-waste may be collected in medical waste containers, e.g. bed pans, catheter bags, fluid canisters, etc. Such waste may contain contaminants, particularly by e.g. virus' or bacteria. Also, in connection with cancer treatment, such waste may be contaminated by radiation.

When the waste has been collected in such medical water containers, medical staff disposes of the waste by emptying the medical waste containers into a waste fixture, e.g. a sink, wash basin, toilet or urinal. Consequently, there is a great risk that the waste is exposed to the atmosphere or splatters on and around undesired locations, including the medical staff, which handles the medical waste containers. This may give rise to the spreading of potentially infectious diseases, or radioactivity, resulting in a hazardous environment.

SUMMARY OF THE INVENTION

An object of the present invention is to avoid the above mentioned drawbacks and to achieve an efficient and environmentally safe method and installation to handle medical waste, bio-waste and other corresponding contaminated waste which limits the transmission of virus', bacteria, and radioactive contaminants particularly in hospitals and medical institutions. The object of the invention is attained by methods and installations disclosed herein.

The basic idea of the invention is to provide an isolated handling of the collected waste. This is realized by employing a vacuum waste system, whereby the medical waste is collected in the receptacle for medical waste, medical waste is discharged from the receptacle for medical waste into a waste fixture connected to a vacuum waste piping of the vacuum waste system. The discharge sequence of the vacuum waste system is activated by an activating means for discharge of the medical waste from the waste fixture or the vacuum waste piping of the vacuum waste system to a waste collecting unit of the vacuum waste system. This ensures that any contaminated waste does not spread into the surroundings or onto the handling staff.

An example of an advantageous receptacle for medical waste is a bed pan, whereby the bed pan is emptied into the waste fixture, after which the discharge sequence is activated in order to discharge the medical waste from the waste fixture. The waste fixture is preferably a sink, wash basin, urinal, toilet or other corresponding unit.

An advantageous alternative for the receptacle for medical waste is a catheter bag, whereby the catheter bag is connected to the waste fixture by means of at least one valve, and in which method the at least one valve is opened in order to provide a flow connection from the catheter bag to the waste fixture. This further enhances the isolated handling of the waste.

The catheter bag is provided with a first valve and a conduit connected to the first valve. In this case, the waste fixture is advantageously a vacuum pipe section, which is connected to the vacuum waste piping, and wherein the waste fixture is provided with a second valve.

BRIEF DESCRIPTION OF THE DRAWING

In the following one embodiment of the present invention will be described, by example only, referring to the attached schematic drawing, in which.

DETAILED DESCRIPTION

This exemplary embodiment illustrates the handling of medical waste that has been collected in a receptacle for medical waste, in this embodiment a catheter bag, which functions as a collection bag.

Figure 1:
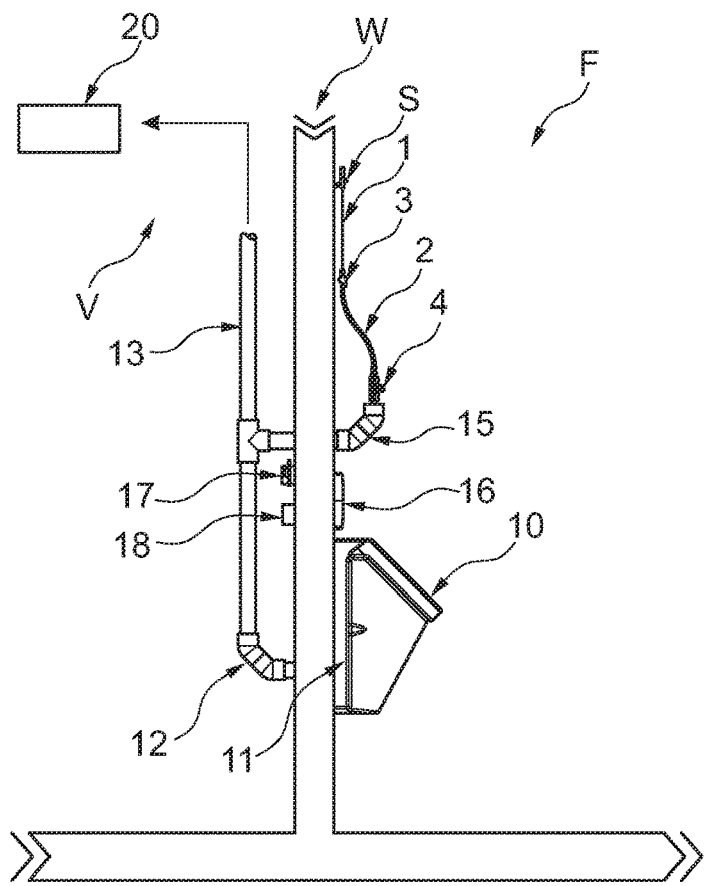
FIG. 1 shows an embodiment of the installation arranged in a facility.
Figure 2:
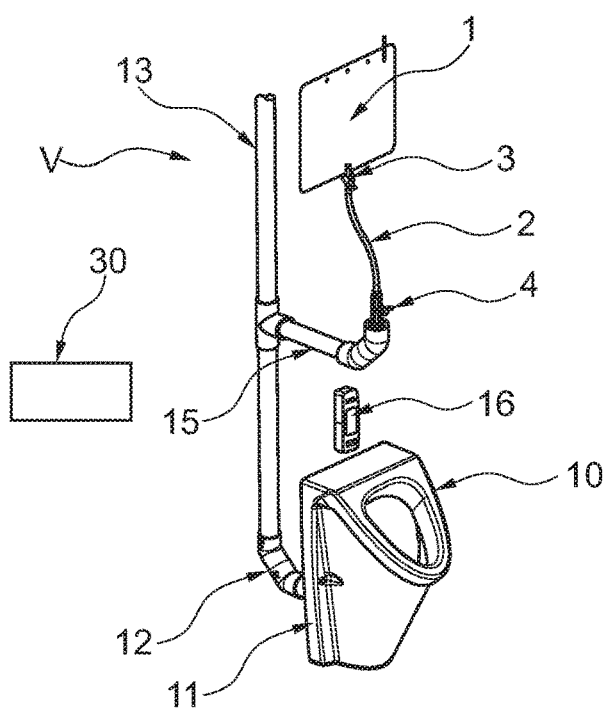
FIG. 2 shows a perspective view of the main components of the installation.

In FIGS. 1 and 2 the catheter bag is indicated by reference numeral 1. A conduit 2, having a first end and a second end, opposite the first end, is connected at said first end to the catheter bag 1 by means of a first valve 3, located at an outlet of the catheter bag 1. The second end of the conduit is connected to a waste fixture, i.e. a vacuum pipe section 15, by means of a second valve 4.

The vacuum pipe section 15 is connected to the vacuum waste system V.

In this embodiment, the vacuum waste system V includes an additional waste fixture, in this case a wall mounted urinal 10. The urinal 10 is connected to a vacuum waste piping 13 by means of a vacuum discharge valve, indicated by reference numeral 11. The vacuum discharge valve 11, located in the backside of the urinal, is of a known type used in typical vacuum waste systems. The discharge valve 11 is connected to an upwards connection 12 of the vacuum waste piping 13. Vacuum is generated in the vacuum waste piping by a vacuum generating means (not shown) typical for a vacuum waste system. The vacuum waste piping 13 leads to a waste collecting unit, e.g. a waste collecting unit 20 or a vacuum center. This is well known in the art and is therefore not described in any detail in this connection.

The vacuum waste system V further includes an activating means for activating a discharge sequence of the urinal, in this case an auto flushing sensor 16. In connection with the auto flushing sensor there is an auto flushing sensor power supply 17 and an auto flushing sensor control unit 18 for the operation of the auto flushing sensor. These are also well known in the art and are therefore not described in any detail in this connection.

As indicated above, the urinal 10 is mounted on a wall W of a facility F. The relevant components of the installation for handling the waste are arranged on the facility side of the wall W. The vacuum pipe section 15 passes through the wall W and is connected to the vacuum waste piping 13 arranged on the opposite side of the wall with respect to the facility F.

The additional waste fixture, i.e. the urinal as discussed above, can be replaced by alternative units such as a toilet bowl, wash basin, sink, or other waste receiving unit, etc., that are compatible with and connectable to a vacuum waste system.

The components of the installation as discussed below are advantageously suitable for medical environments and suitable for vacuum systems.

In general, the installation is used as follows. After the waste has been collected in the catheter bag 1, the medical staff relieves a patient of the catheter bag 1 provided with the first valve 3 and the conduit 2. The medical staff then hangs the catheter bag 1 on a support S provided on the wall W of the facility F and connects the conduit 2 to the second valve 4. Subsequently, the second valve 4 is connected in an appropriate manner to the vacuum pipe section 15. The second valve 4 is advantageously permanently affixed to the vacuum pipe section. The first valve 3 and the second valve 4 can then be opened, which will result in that the contents of the catheter bag 1 will be discharged into the vacuum waste piping 13 through the vacuum pipe connection 15. After the catheter bag has been emptied, the first valve 3 can be closed. The second valve 4 is closed and the conduit 2 is disconnected from the second valve 4. The catheter bag, with the first valve and the conduit, can be disposed of into a safe disposal unit. The first valve and the second valve are advantageously one-way valves in order to avoid return flow.

In a normal operational mode of the vacuum waste system, a partial vacuum prevails in the vacuum waste piping 13, including in this case the upwards connections 12, i.e. after the discharge valve 11 in the flow direction of waste.

When the medical staff moves away from the installation, the auto flushing sensor 16 mounted on the wall W activates a flushing sequence, which flushes the urinal 10 creating a vacuum based discharge flow in the vacuum waste piping 13, as well as in the vacuum pipe section 15. This transports the waste, including the medical waste from the catheter bag 1, towards e.g. a collecting unit 20.

Consequently, the waste collected in the catheter bag is drained from the catheter bag without any exposure to the atmosphere and without coming into contact with anything within the facility and is further transported to e.g. an appropriate waste collecting tank in the same manner. In other words, the waste is collected and disposed of without said waste being exposed to the environment surrounding the catheter bag.

The urinal, or any other corresponding additional waste fixture as mentioned above, is a helpful and practical additional device, also functioning as a safe guard, in such an installation. Conventional bed pans, which function as a collection device, schematically illustrated in FIG. 1 by reference numeral 30, can be emptied into the urinal, whereby waste from such bed pans can conveniently be disposed of into the vacuum waste system.

The drawings and the description related thereto are only intended for clarification of the basic idea of the invention. The invention, including the main components comprising the catheter bag, the valves, the conduit, the waste fixture, the vacuum center, piping and valves, etc. may vary in detail within the scope of the ensuing claims.

The invention claimed is:

1. A method for handling a medical waste, the method comprising:

collecting the medical waste in a disposable receptacle, wherein the disposable receptacle comprises a bag and a conduit coupled to the bag by a first valve;

providing a vacuum waste system, comprising:
 a waste collecting unit;
 a vacuum waste piping extending upwardly toward and in fluid communication with the waste collecting unit, wherein the vacuum waste piping is maintained under vacuum;
 a vacuum pipe section in fluid communication with the vacuum waste piping;
 a waste pipe section in fluid communication with the vacuum waste piping; and
 a second valve coupled to the waste pipe section and configured to releasably couple to the conduit;

connecting the conduit to the second valve;

selectively opening the first valve and the second valve to communicate vacuum from the vacuum waste piping to the bag, thereby to transfer the medical waste from the disposable receptacle to the vacuum waste piping; and activating a discharge sequence of the vacuum waste system by an activating means for discharge of the medical waste from the vacuum waste piping to the waste collecting unit.

2. The method according to claim 1, wherein the disposable receptacle comprises a disposable catheter bag.

3. The method according to claim 1, wherein the vacuum waste system comprises an additional waste fixture.

4. An installation, comprising:

a disposable receptacle for receiving a medical waste, the disposable receptacle including:
 a bag; and
 a conduit coupled to the bag by a first valve; and a vacuum waste system, comprising:
 a waste collecting unit;
 a vacuum waste piping extending upwardly toward and in fluid communication with the waste collecting unit, wherein the vacuum waste piping is maintained under vacuum;
 a waste pipe section in fluid communication with the vacuum waste piping;
 a second valve coupled to the waste pipe section and configured to releasably couple to the conduit; and
 an activating means for activating a discharge sequence of the vacuum waste system;

wherein, when the conduit of the disposable receptacle is coupled to the second valve, and with the first and second valves open, vacuum from the vacuum waste piping is communicated to the bag to transfer the medical waste from the disposable receptacle to the vacuum waste piping; and wherein activation of the activation means transfers the medical waste from the vacuum waste piping to the waste collecting unit.

5. The installation according to claim 4, wherein the disposable receptacle comprises a disposable catheter bag.

6. The installation according to claim 4, wherein each component of the installation is medical rated, approved for use in medical facilities, and/or vacuum rated.

7. The installation according to claim 4, wherein the installation comprises an additional waste fixture connected to the vacuum waste system.

* * * * *